(12) United States Patent
Chang et al.

(10) Patent No.: US 9,110,166 B2
(45) Date of Patent: Aug. 18, 2015

(54) ACOUSTIC IMAGING

(75) Inventors: Chung Chang, Houston, TX (US); Arthur Cheng, Houston, TX (US); Chen Li, Katy, TX (US); Steve Zannoni, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 829 days.

(21) Appl. No.: 13/309,342

(22) Filed: Dec. 1, 2011

(65) Prior Publication Data

US 2013/0142009 A1    Jun. 6, 2013

(51) Int. Cl.
| | | |
|---|---|---|
| *G01S 15/89* | (2006.01) | |
| *G01N 29/22* | (2006.01) | |
| G03B 42/06 | (2006.01) | |
| A61B 8/08 | (2006.01) | |
| G01V 1/38 | (2006.01) | |

(52) U.S. Cl.
CPC .......... *G01S 15/8977* (2013.01); *G01N 29/221* (2013.01); *G01S 15/8997* (2013.01); *A61B 8/5207* (2013.01); *G01V 1/38* (2013.01); *G03B 42/06* (2013.01)

(58) Field of Classification Search
CPC ........ G01V 1/38; A61B 8/5207; G03B 42/06; G01S 15/8977; G01S 15/8998; G01N 29/221
USPC .......................................................... 367/73
See application file for complete search history.

(56) References Cited

U.S. PATENT DOCUMENTS

| | | | |
|---|---|---|---|
| 3,675,472 A | 7/1972 | Kay | |
| 4,597,292 A | 7/1986 | Fujii et al. | |
| 5,186,177 A | 2/1993 | O'Donnell et al. | |
| 5,329,930 A * | 7/1994 | Thomas et al. | 600/447 |
| 5,428,999 A | 7/1995 | Fink | |
| 5,476,010 A * | 12/1995 | Fleming et al. | 73/620 |
| 5,720,708 A | 2/1998 | Lu et al. | |
| 5,891,038 A | 4/1999 | Seyed-Bolorforosh et al. | |
| 5,999,488 A | 12/1999 | Smith | |
| 6,506,171 B1 | 1/2003 | Vitek et al. | |
| 7,090,641 B2 | 8/2006 | Biagi et al. | |
| 2004/0158404 A1 | 8/2004 | Gaston et al. | |
| 2005/0139006 A1 | 6/2005 | Lorraine et al. | |
| 2006/0175057 A1 | 8/2006 | Mandal et al. | |

(Continued)

FOREIGN PATENT DOCUMENTS

WO    WO-2013/082480 A1    6/2013

OTHER PUBLICATIONS

Elbern, SAFT technique for image restauration, NDT.net, Aug. 2000, vol. 5 , No. 08, pp. 1-6.*

(Continued)

*Primary Examiner* — Luke Ratcliffe
*Assistant Examiner* — Hovhannes Baghdasaryan
(74) *Attorney, Agent, or Firm* — Schwegman Lundberg & Woessner, P.A.; Benjamin Fite (57) ABSTRACT

In various embodiments, apparatus and methods are provided to perform acoustic imaging. An acoustic wave can be acquired at a detector, where the acoustic wave propagates from a target to the detector. The target may be acoustically illuminated to provide the acoustic wave. A signal from the detector in response to acquiring the acoustic wave can be processed in a model such that the processing implements a synthetic acoustic lens to generate an image of the target. Additional apparatus, systems, and methods are disclosed.

30 Claims, 7 Drawing Sheets

200

ACQUIRE AN ACOUSTIC WAVE AT A DETECTOR, THE ACOUSTIC WAVE PROPAGATING FROM A TARGET TO THE DETECTOR

210

PROCESS, IN A MODEL, A SIGNAL FROM THE DETECTOR IN RESPONSE TO ACQUIRING THE ACOUSTIC WAVE SUCH THAT THE PROCESSING IMPLEMENTS A SYNTHETIC ACOUSTIC LENS TO GENERATE AN IMAGE OF THE TARGET

220

(56) References Cited

U.S. PATENT DOCUMENTS

2008/0121040 A1* 5/2008 MacLauchlan et al. ........ 73/618
2008/0190169 A1   8/2008 Naum et al.
2008/0314582 A1* 12/2008 Belani et al. ................. 166/113
2008/0316860 A1* 12/2008 Muyzert et al. ................ 367/25
2009/0312997 A1* 12/2009 Freed et al. .................... 703/10

OTHER PUBLICATIONS

"International Application Serial No. PCT/US2012/067373, International Search Report mailed Mar. 28, 2013", 3 pgs.
"International Application Serial No. PCT/US2012/067373, Written Opinion mailed Mar. 28, 2013", 8 pgs.
"International Application Serial No. PCT/US2012/067373, International Preliminary Report on Patentability mailed Mar. 11, 2014", 9 pgs.
"International Application Serial No, PCT/US2012/067373, Response filed Sep. 20, 2013 to Written Opinion mailed Mar. 28, 2013", 2 pgs.
"Australian Application Serial No. 2012345736, First Examiner Report mailed Aug. 19, 2014", 2 pgs.
"European Application Serial No. 12852608.4, Office Action mailed Jul. 15, 2014", 3 pgs.
"European Application Serial No. 12852608.4, Reply filed Jul. 31, 2014 to Office Action mailed Jul. 15, 2014", 10 pgs.
"European Application No. 12852608.4, Extended European Search Report mailed Apr. 30, 2015", 9 pgs.
"Mexican Application No. MX/a/2014/006392, Office Action mailed Apr. 30, 2015", (w/English Summary), 3 pgs.
Jin, S., et al, "Visibility analysis for target-oriented reverse time migration and optimizing acquisition parameters", The Leading Edge, 29(11), (Nov. 2010), 1372-1377.

* cited by examiner

ACOUSTIC IMAGING

TECHNICAL FIELD

The invention relates generally to methods and apparatus for imaging.

BACKGROUND

High quality acoustic images can be formed by using acoustic illumination and acoustic lens. For example, in a pitch-catch mode of operation, an acoustic wave generated from an acoustic source is reflected from a target to an acoustic lens that directs the reflected acoustic wave to a detector. Different acoustic target depths can be imaged by adjusting the acoustic focal distance of the acoustic lens. In another pitch-catch arrangement, the acoustic lens and the detector are arranged at opposite sides of the target from the acoustic source. This mode operates in a transmission mode of acquisition. Systems using acoustic lens in these arrangements have been commercialized with applications to medical and aerospace imaging systems for examinations. However, there are a few handicaps in ultrasonic imaging devices such as ultrasonic cameras due to limited source and receiver apertures and the physical size of the available acoustic lenses, as well as impedance contrast of these acoustic lenses. It is also noted that the oilfield service industry has not explored the full potential of ultrasonic imaging system due to several technical and knowledge bottlenecks.

BRIEF DESCRIPTION OF THE DRAWINGS

Embodiments of the invention are illustrated by way of example and not limitation in the figures of the accompanying drawings in which.

DETAILED DESCRIPTION

The following detailed description refers to the accompanying drawings that show, by way of illustration and not limitation, various embodiments in which the invention may be practiced. These embodiments are described in sufficient detail to enable those skilled in the art to practice these and other embodiments. Other embodiments may be utilized, and structural, logical, and electrical changes may be made to these embodiments. The various embodiments are not necessarily mutually exclusive, as some embodiments can be combined with one or more other embodiments to form new embodiments. The following detailed description is, therefore, not to be taken in a limiting sense.

In various embodiments, an acoustic full array waveform imaging system can be implemented that is straightforward and robust to expand acoustic imaging to borehole applications. The imaging system can be structured to perform imaging by processing data collected from acoustic waveforms incident on a detector. The acoustic imaging can be conducted without use of a physical acoustic lens. This imaging can include effective focusing of the acoustic waveform by using a model to process waveform parameters from the detector without using a physical acoustic lens. The acoustic imaging can be realized as ultrasonic imaging. This technique and apparatus can be applied to medical imaging as well as marine seismic survey in different frequency and scale range. The imaging system can be discussed in terms of the imaging analogy between acoustic waves and light waves when wavelengths of interest are shorter than the target reflector.

Figure 1A:
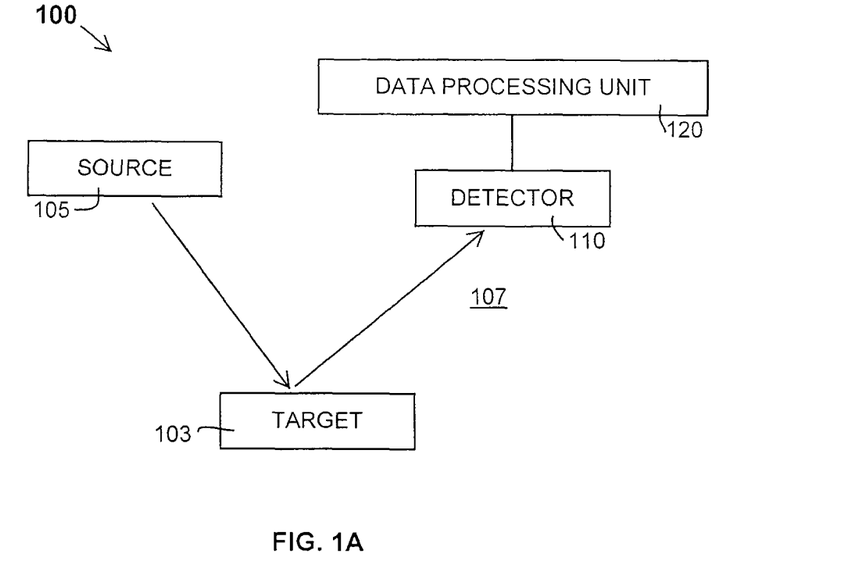
FIG. 1A shows a block diagram of an example system having a source of acoustic illumination and a detector to receive an acoustic wave from a target, in accordance with various embodiments.
Figure 1B:
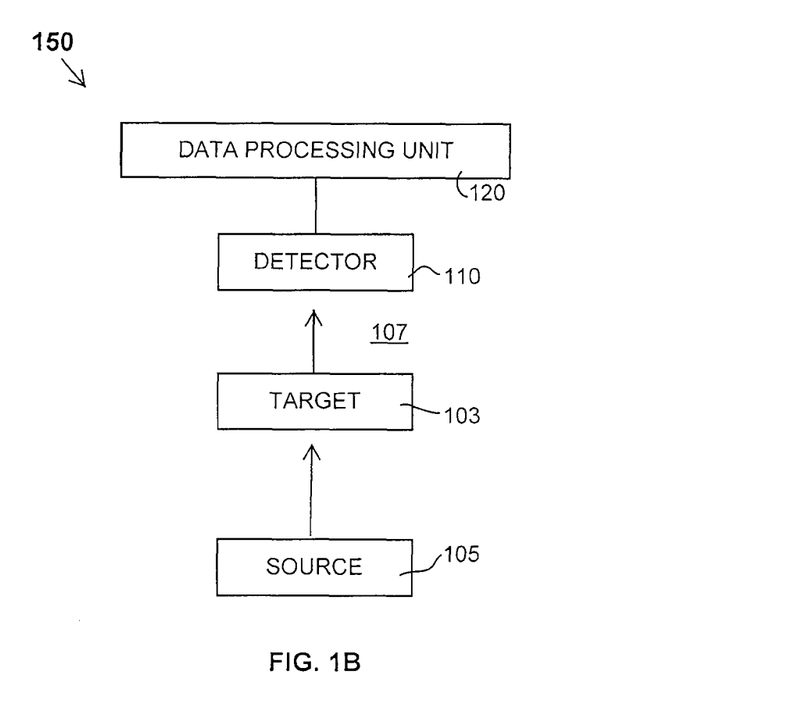
FIG. 1B shows a block diagram of an example system having a source of acoustic illumination and a detector to receive an acoustic wave from a target in a transmission mode, in accordance with various embodiments

FIG. 1A shows a system 100 having a source 105 of acoustic illumination and a detector 110 to receive an acoustic wave from a target 103. The source 105 can be provided by an acoustic transducer. The detector 110 can be structured as an array of sensors. Output from the detector 110 can be sent to a data processing unit 120 that operates to generate synthetic focusing and acoustic lenses. By synthetic focusing and synthetic acoustic lens, it is meant that the focusing and the acoustic lens are generated by processing the acoustic waveforms received by a detector, rather than being a physical focusing and physical acoustic lens. FIG. 1B shows system 150 with the source 105 of acoustic illumination and the detector 110 to receive an acoustic wave from the target 103 in a transmission mode.

The medium 107 between the target 103 and the detector 110 provides an acoustic buffering layer 107. The acoustic buffering layer 107 can be a buffering fluid. The acoustic buffering layer 107 can be used to obtain a reflected pressure wave field either in pulse-echo mode or in pitch-catch mode, each with an appropriate recording time window at a specified offset plane from the target reflector 103. In pulse-echo mode, a transducer operates as both the source and the detector of pulsed waves as the acoustic wave is reflected back to the transducer. The detector 110 can include a planar array of individually digitized pressure sensors. The pressure wave field can be recorded by the detector 110 or by the data processing unit 120.

By controlling the source 105, the acoustic illumination is repeatable. Since the acoustic illumination is repeatable, a large receiver array aperture can be synthesized by physically moving the detector 110, such as a receiver array, and repeating the acoustic illumination from the source 105. This allows a large receiver array aperture to be used without using very large physical array of receivers for the detector 110.

To completely describe the reflected wave field, the same measurement using the source 105 can be repeated at an incremental offset to derive the particle velocity wave field from the pressure gradient calculations. The incremental offset is a difference in position of the detector 110 provided by moving the detector 110. This derivation can be conducted according to the following equation with pressure variable p, velocity variable v, and fluid density $\rho_0$:

$$-\nabla p - \rho_0 \frac{\partial v}{\partial t}.$$

This calculation may be facilitated by moving the detector plane in one direction along the propagation path of the acoustic wave. With both the reflected pressure wave field and the velocity wave field at the same receiving plane acquired, these recorded array signals can be used to forward propagate the wave fields inside a model. The model can be realized as a finite difference model. The model can be structured to evaluate an acoustic in a manner similar to evaluating an optical wave in an optical imaging system.

With detector 110 having a effective aperture and with the source 105 controlled to provide sets of acoustic waves at different wavelengths, instructions for the model, physically in a data storage device, can be executed by one or more processors to generate an effective focusing of the received acoustic waves. The model can be executed to generate an effective acoustic lens. The model can be arranged to have perfect or essentially perfect matching boundary layers with the buffering layer 107 without creating reflections from the model boundaries and to have the same mechanical properties as the buffering layer 107. In the model, a number of acoustic lenses of different shapes and contrast can be implemented. These modeled lenses, also referred herein to as synthetic lenses, can optimize and improve the target images at different depths of the target 103. Acoustic images can be formed by calculating the acoustic pressure intensity at a planar cell array near the focal point inside the model, such as a finite difference model, and by converting the intensity amplitude to optical gray scale levels to form optical images at different depths. This technique allows for imaging without sophisticated migration and inversion schemes to an optical image as well as for operation without a physical acoustic lens to form the video of the target generating the acoustic images.

Figure 2:
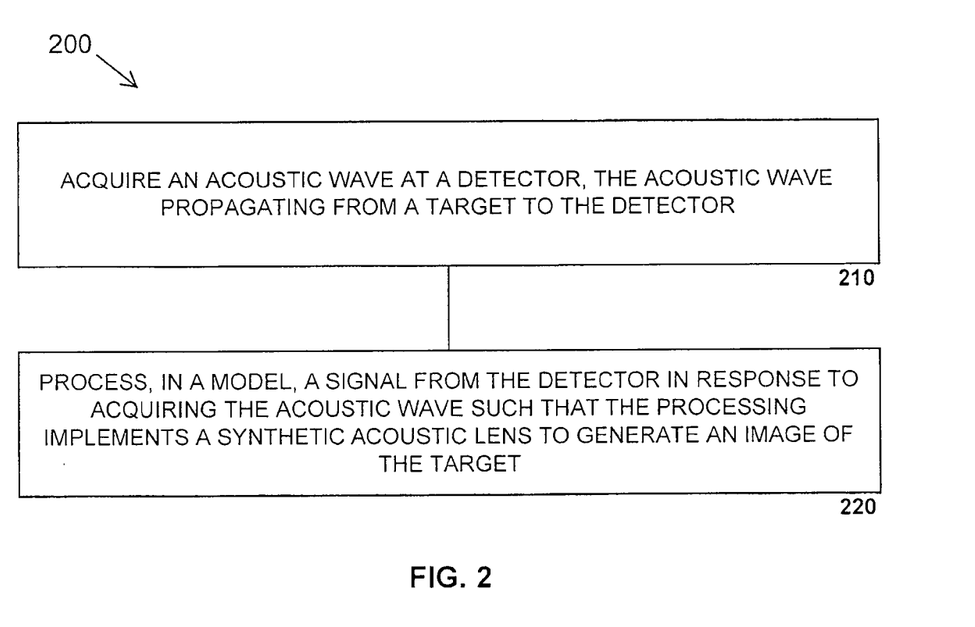
FIG. 2 illustrates features of an example method of acoustic imaging without using an acoustic lens, in accordance with various embodiments.

FIG. 2 shows features of an example embodiment of a method 200 of acoustic imaging without using an acoustic lens. At 210, an acoustic wave is acquired at a detector, where the acoustic wave has propagated from a target to the detector. The target can be acoustically illuminated to provide the acoustic wave. It is noted that the acoustic wave may also be referred to as an acoustic signal. Controlling a source to selectively illuminate a target at different wavelengths allows for the imaging system to acquire and operate on acoustic signals of different wavelengths, subsequently providing for enhanced imaging. Acquiring the acoustic wave at the detector can include acquiring the acoustic wave at a planar array of individual pressure sensors. Method 200 can include synthesizing a receiver array aperture larger than that of the planar array of individual pressure sensors by physically moving the planar array and repeating the acoustic illumination of the target and acquisition of an acoustic wave from the target. Moving the planar array may be accomplished with a motor such as micro-motor.

At 220, in a model using a processor, a signal from the detector in response to acquiring the acoustic wave is processed such that the processing implements a synthetic acoustic lens to generate an image of the target. The generated image can be shown on a display. The image can be formed by calculating acoustic pressure intensity amplitude at a planar cell array near a focal point inside the model and by converting the intensity amplitude to an optical gray scale level. The model can be structured as a finite difference model. The model can be structured to have perfect or essentially perfect matching boundary layers with a buffering layer through which the acoustic wave propagates from the target to the detector and to have mechanical properties of the buffering layer. The processing can include implementing a plurality of synthetic acoustic lenses of different shapes and contrast such that target images at different depths of the target are generated.

The method 200 can include: operating on the detector such that an incremental offset of the detector relative to the target is generated, where the starting plane for the incremental offset relative to the detector corresponds to when the acoustic wave is acquired; acquiring a second acoustic wave at the detector, the second acoustic wave propagating from the target to the detector; deriving a velocity wave field based on a pressure gradient calculation using acquired acoustic waves at the detector; and applying a pressure wave field of the acoustic wave and the velocity wave field in the processing in the model to generate the image of the target.

The method 200 can include: using a planar array of individual pressure sensors as the detector to generate a pressure wave field; using velocity sensors to directly record a velocity wave field; and applying the pressure wave field and the velocity wave field in the processing in the model to generate the image of the target. In addition, the method 200 can be conducted with respect of an oil or gas drilling operation.

In various embodiments, modifications to this technique can be made according to the environment of the application to which the acoustic technique is being applied. For example, in marine seismic acquisition, the velocity wave field can be directly recorded with velocity sensors. Therefore, the offset pressure measurement to derive the particle velocity wave field may be skipped in implementing this embodiment of an acoustic imaging technique.

Figure 3:
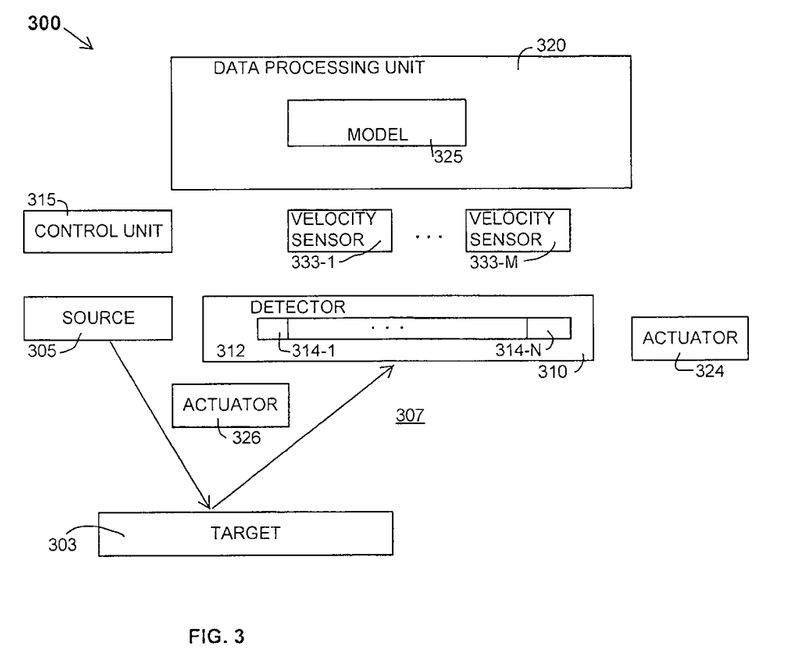
FIG. 3 shows a block diagram of a system having functionality to perform acoustic imaging, in accordance with various embodiments.

FIG. 3 shows a block diagram of a system 300 having functionality to perform acoustic imaging. The system 300 can include a detector 310 to acquire acoustic waves from a target 303 and a data processing unit 320 to generate an image of the target. The data processing unit 320 can be arranged to process signals from the detector 310 in response to the acquired acoustic waves and can be arranged to process the signals in a model 325 such that the data processing unit 320 operatively implements a synthetic acoustic lens to generate the image of the target. The system 300 may include a source 305 to acoustically illuminate the target. The source 305 can be structured as one or more conventional transducers. The system 300 also may include a control unit 315 to control the detector 310 and the source 305.

The data processing unit 320 can be structured to generate the image by operatively calculating acoustic pressure intensity amplitude at a planar cell array near a focal point inside the model 325 and by operatively converting the intensity amplitude to an optical gray scale level. The data processing unit 320 can be structured to implement a plurality of synthetic acoustic lenses of different shapes and contrast to operatively generate target images at different depths of the target 303. The data processing unit 320 can be operated in conjunction with the control unit 315 to conduct a number of repeatable measurements at different acoustic wavelengths. The data processing unit 320 and the control unit 315 can structured as separate units or as a single unit. The model 325 can be structured to generate perfect or essentially perfect matching boundary layers with a buffering layer 307 through which the acoustic wave propagates from the target 303 to the detector 310 and to generate mechanical properties of the buffering layer 307.

The detector 310 can include a planar array 312 of individual pressure sensors 314-1 ... 314-N. The system 300 can also include actuators 324 and 326 to operate with the detector 310 of the planar array 312. The actuator 324 can be arranged to physically move the planar array 312 such that the data processing unit 320 is enabled to operatively synthesize a receiver array aperture larger than that of the planar array 312. The actuator 326 can be arranged to physically move the planar array 312 to generate an incremental offset of the detector 310 relative to the target 303 such that the data processing unit 320 is enabled to operatively derive a velocity wave field based on a pressure gradient calculation using acquired acoustic waves at the detector 310 and to apply the velocity wave field and a corresponding pressure wave field in the processing in the model to generate the image of the target 303. The enablement of the data processing unit 320 can be provided by collecting data on which the data processing unit 320 can operate. Optionally, the system 300 can include one or more velocity sensors 333-1 . . . 333-M structured to directly record a velocity wave field to be used in the generation of the image of the target 303. The use of the velocity sensors 333-1 . . . 333-M can reduce the workload of the data processing unit 320 and actuator 326.

The detector 310 and the data processing unit 320 can be arranged as a number of different tools. The detector 310 and the data processing unit 320 can be arranged as a logging-while-drilling tool. The detector 310 and the data processing unit 320 can be arranged as a wireline tool. The detector 310 and the data processing unit 320 can be arranged as a medical imaging tool. The detector 310 and the data processing unit 320 also can be arranged as a marine seismic survey tool. The system 300 including the detector 310 and the data processing unit 320 can be arranged in imaging structures in a variety of different applications in different technical fields.

Figure 4:
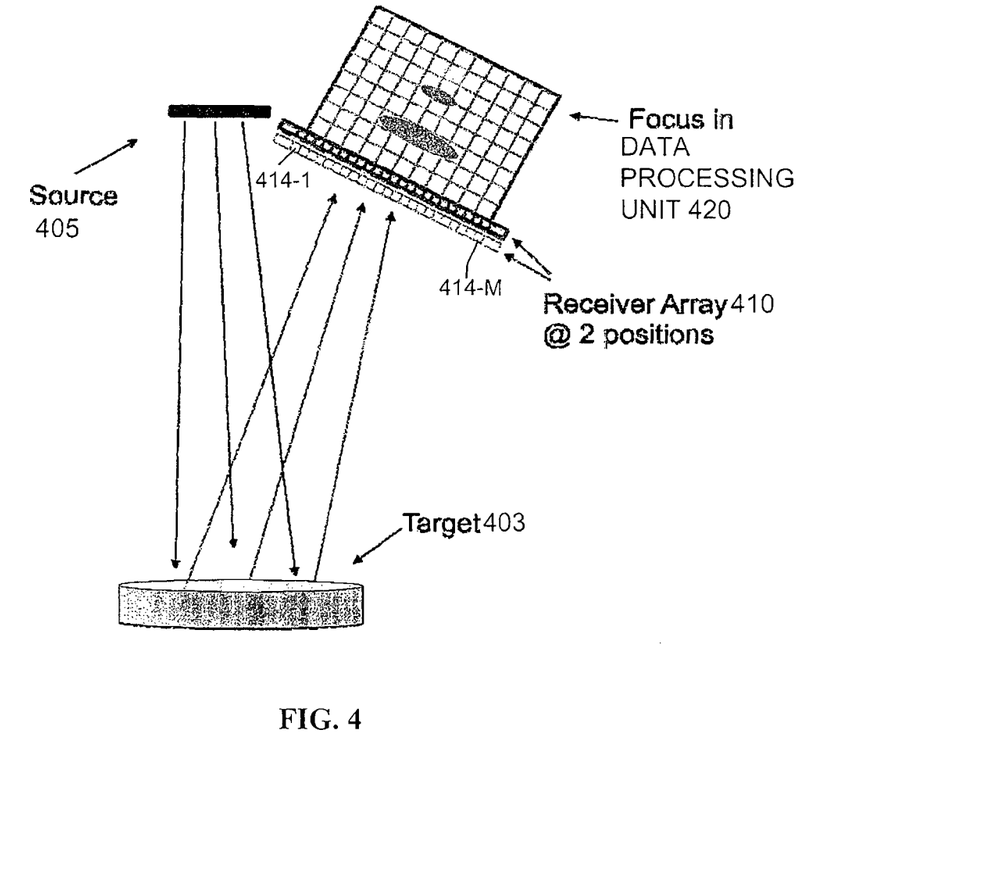
FIG. 4 illustrates operation on a planar array of sensors to provide an incremental offset relative to a target, in accordance with various embodiments.

FIG. 4 illustrates operation on a planar array 410 of sensors 414-1 . . . 414-M to provide an incremental offset relative to a target 403 to derive a particle velocity wave field from pressure gradient calculations. The planar array 410 of sensors can be structured as individually digitized pressure sensors. The source 405 generates an acoustic wave directed at the target 403, which is reflected to the planar array 410 with the planar array 410 at a first position. The source 405 generates an acoustic wave directed at the target 403, which is reflected to the planar array 410 with the planar array 410 at a second position. With the sensors 414-1 . . . 414-M transmitting a signal to the data processing unit 420 with the planar array 410 at both the first and second positions, the data processing unit 420 can derive the particle velocity wave field using pressure gradient calculations. Such an incremental procedure can also be used with source 405 and planar array 410 in a transmission mode.

Various components of a system include a tool having a detector arranged to detect acoustic waves and a data processing unit arranged to process signals from the detector in response to the acquired acoustic waves, where the data processing unit can be arranged to process the signals in a model such that the data processing unit operatively implements a synthetic acoustic lens to generate an image of a target from which the acoustic wave was received. A system including such a tool, as described herein or in a similar manner, can be realized in combinations of hardware and software based implementations. These implementations may include a machine-readable storage device having machine-executable instructions, such as a computer-readable storage device having computer-executable instructions, to operate the tool. The machine-readable storage device can have instructions stored thereon, which, when executed by a machine, cause the machine to perform operations, the operations comprising: acquiring a signal from a detector in response to the detector acquiring an acoustic wave, the acoustic wave propagating from a target to the detector, the target being acoustically illuminated to provide the acoustic wave; and processing, in a model using a processor, the signal from the detector in response to acquiring the acoustic wave such that the processing implements a synthetic acoustic lens to generate an image of the target. The instructions can include instructions to perform operations similar to or identical to the operations related to method 200 and other processes discussed herein. The instructions can also include instructions to operate sensors, a control unit, and a data processing unit in accordance with the teachings herein. Further, a machine-readable storage device, herein, is a physical device that stores data represented by physical structure within the device. Examples of machine-readable storage devices include, but are not limited to, read only memory (ROM), random access memory (RAM), a magnetic disk storage device, an optical storage device, a flash memory, and other electronic, magnetic, and/or optical memory devices. The data processing unit can be realized as an integrated structure having one or more processors and one or more memory units. The data processing unit may be realized as a computer with stored instructions providing a model, such as a finite difference model. Alternatively, a system can include one or more processors, one or more memory units, and other instrumentalities that have, as a portion of their functionalities, the tasks of the data processing unit, and optionally the control of the detectors of the tool and sources used in the various techniques, to perform acoustic imaging in accordance with the teachings of methods and apparatus discussed herein.

In various embodiments, data processing of received acoustic signals, without using an acoustic lens, can replace acoustic lens focusing and imaging conversion hardware. The capability to synthesize a large array and different acoustic lenses can provide for improving image quality and relaxing the array aperture size limitation. These techniques, as discussed herein, may achieve image quality and resolution that are previously unachievable, fast imaging capability without using sophisticated inversion, three-dimensional (3D) object viewing, and acoustic imaging using a narrow frequency band source. Other enhancements to acoustic imaging may be obtained. In addition, these techniques, as discussed herein, can be used in a variety of applications.

Figure 5:
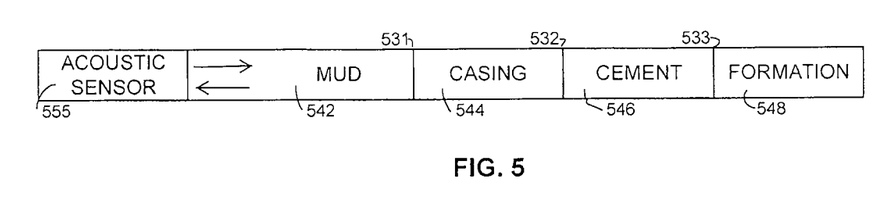
FIG. 5 depicts a block diagram of an example acoustic sensor system to evaluate a cased hole cement structure, in accordance with various embodiments.

In an embodiment, the technique can be used in a wireline application in an open hole to image open fractures and fine fractures hidden underneath a mud cake. Typically, a wireline operation is related to an aspect of logging that employs a cable to lower tools into a borehole and to transmit data. In addition to wireline applications, embodiments as discussed herein can be used in measurements-while-drilling (MWD) systems such as a logging-while-drilling (LWD) system. In another embodiment, the technique can be used in an evaluation of cased hole cement as illustrated in FIG. 5. For evaluation of cased hole cement, the evaluated structure can include a first interface 531 between mud 542 and a casing 544, a second interface 532 between the casing 544 and cement 546, and a third interface 533 between the cement 546 and a formation 548. With a source generating an acoustic signal into the mud 542 towards the formation 548, a pitch-catch configuration of the source and the detector of acoustic sensor system 555 can be used to conduct third interface imaging.

Figure 6:
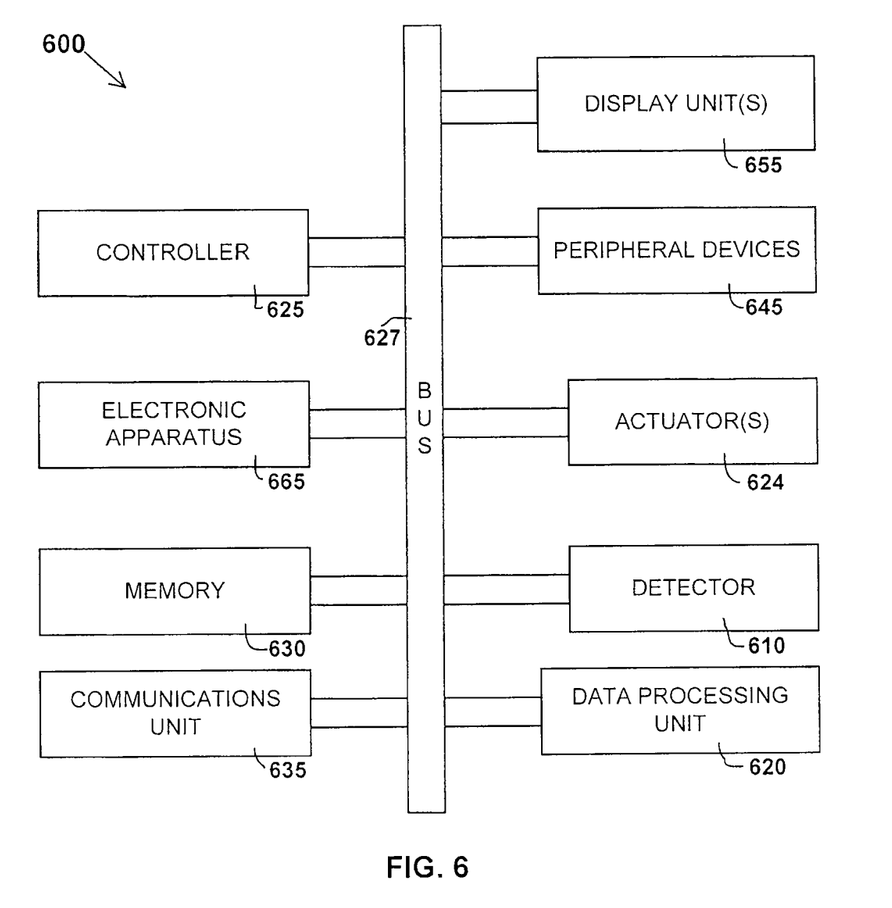
FIG. 6 depicts a block diagram of features of an example system to perform acoustic imaging, in accordance with various embodiments.

FIG. 6 depicts a block diagram of features of an example embodiment of a system 600 having a detector 610 arranged to detect acoustic waves and a data processing unit 620 arranged to process signals from the detector 610 in response to the acquired acoustic waves, where the data processing unit 620 can be arranged to process the signals in a model such that the data processing unit 620 operatively implements a synthetic acoustic lens to generate an image of a target from which the acoustic wave was received. The image can be shown on one or more displays 655. The system 600 can also include one or more actuators 624 to physically move the detector 610. The detector 610 and the data processing unit 620 can be realized in a similar or identical manner to arrangements of detectors and the data processing units discussed herein. The system 600 can be configured to operate in accordance with the teachings herein.

The system 600 can include a controller 625, a memory 630, an electronic apparatus 665, and a communications unit 635. The controller 625, the memory 630, and the communications unit 635 can be arranged to operate as a processing unit to control operation of the detector 610 and to process output from the detector 610 to perform acoustic imaging without a physical acoustic lens using a synthetic lens to image a target in a manner similar or identical to the procedures discussed herein. The data processing unit 620, structured as a standalone unit with its own processors and memory to operate in a manner similar or identical to the procedures discussed herein, may be implemented as a single unit. The data processing unit 620, structured to operate in a manner similar or identical to the procedures discussed herein, may be distributed among the components of the system 600 including the electronic apparatus 665. The controller 625 and the memory 630 can operate to control activation of a source 605 and control positioning of the detector 610 using the one or more actuators 624 and to manage processing schemes in accordance with measurement procedures and signal processing as described herein. The data processing unit 620 and other components of system 600 can be configured, for example, to operate similar to or identical to the components of systems as described herein, or similar to or identical to any of methods described herein.

For operation in an oil or gas drilling operation, the communications unit 635 can include downhole communications for appropriately located sensors. Such downhole communications can include a telemetry system. The communications unit 635 may use combinations of wired communication technologies and wireless technologies at frequencies that do not interfere with on-going measurements.

The system 600 can also include a bus 627, where the bus 627 provides electrical conductivity among the components of the system 600. The bus 627 can include an address bus, a data bus, and a control bus, each independently configured or in an integrated format. The bus 627 can be realized using a number of different communication mediums that allows for the distribution of components of the system 600. Use of the bus 627 can be regulated by the controller 625.

In various embodiments, the peripheral devices 645 can include displays, additional storage memory, or other control devices that may operate in conjunction with the controller 625, the memory 630, or both the controller 625 and the memory 630. In an embodiment, the controller 625 can be realized as a processor or a group of processors that may operate independently depending on an assigned function. The peripheral devices 645 can be arranged with a display, as a distributed component on the surface in a drilling operation, which can be used with instructions stored in the memory 630 to implement a user interface to monitor the operation of the detector 610, the data processing unit 620, and components distributed within system 600. The user interface can be used to input parameter values for thresholds such that the system 600 can operate autonomously substantially without user intervention. The user interface can also provide for manual override and change of control of the system 600 to a user. Such a user interface can be operated in conjunction with the communications unit 635 and the bus 627.

Figure 7:
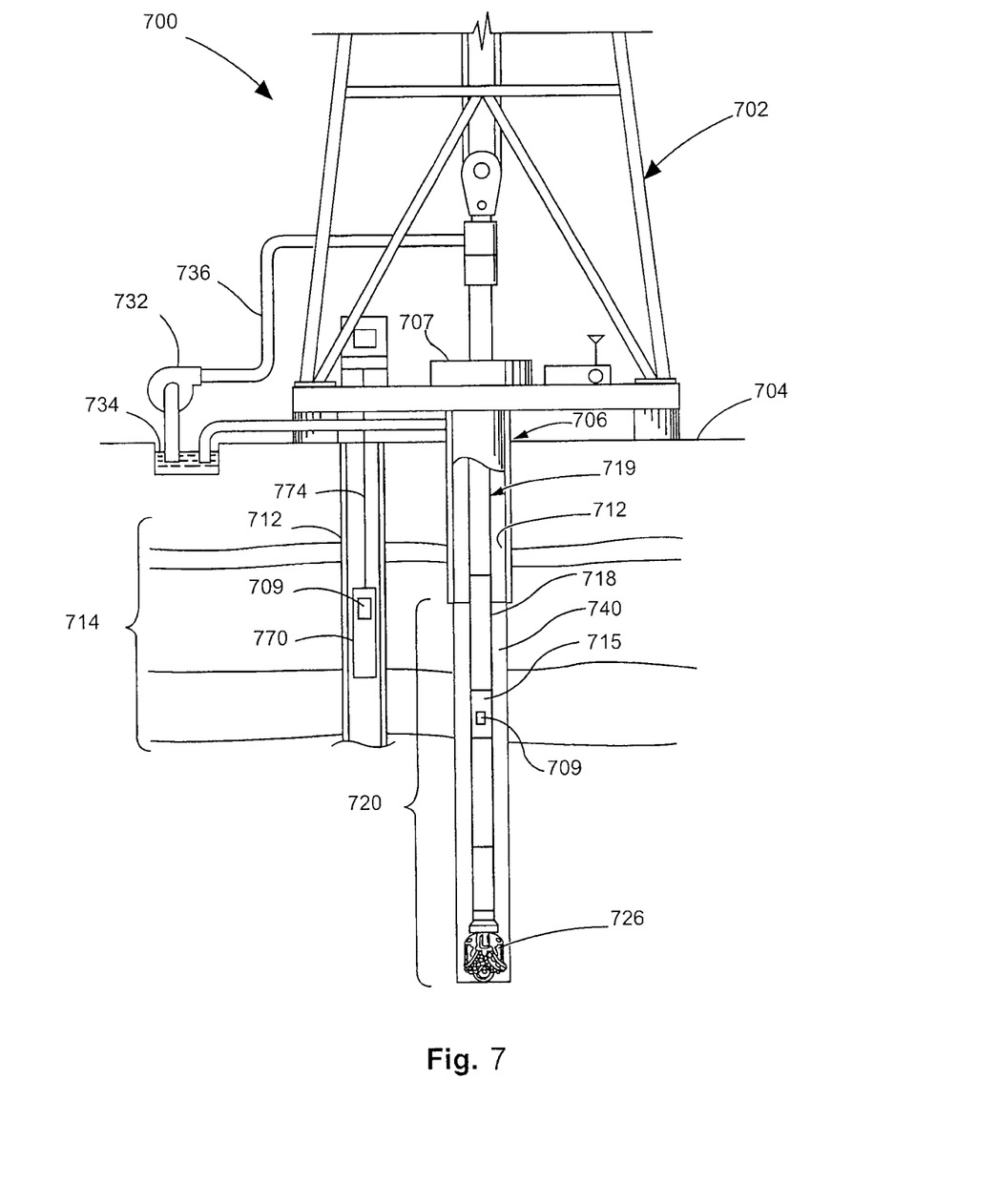
FIG. 7 depicts an example system at a drilling site, where the system includes a tool configured to perform acoustic imaging, in accordance with various embodiments.

FIG. 7 depicts an embodiment of a system 700 at a drilling site, where system 700 includes a tool 709 having a detector arranged to detect acoustic waves and a data processing unit arranged to process signals from the detector in response to the acquired acoustic waves, where the data processing unit can be arranged to process the signals in a model such that the data processing unit operatively implements a synthetic acoustic lens to generate an image of a target from which the acoustic wave was received. The tool 709 can be realized in a similar or identical manner to arrangements of detectors and data processing units discussed herein. The tool 709 can be structured and fabricated in accordance with various embodiments as taught herein with respect to a detector and data processing unit to perform acoustic imaging.

System 700 can include a drilling rig 702 located at a surface 704 of a well 706 and a string of drill pipes, that is, the drill string 708, connected together so as to form a drilling string that is lowered through a rotary table 707 into a wellbore or borehole 712. The drilling rig 702 can provide support for the drill string 708. The drill string 708 can operate to penetrate the rotary table 707 for drilling a borehole 712 through subsurface formations 714. The drill string 708 can include drill pipe 718 and a bottom hole assembly 720 located at the lower portion of the drill pipe 718.

The bottom hole assembly 720 can include a drill collar 715, the tool 709 attached to the drill collar 715, and a drill bit 726. The drill bit 726 can operate to create a borehole 712 by penetrating the surface 704 and the subsurface formations 714. The tool 709 can be structured for an implementation in the borehole of a well as a MWD system such as a LWD system. The housing containing the tool 709 can include electronics to activate one or more acoustic sources of the tool 709 and collect responses from a detector of the tool 709. Such electronics can include a data unit to provide images and analyzed results to the surface over a standard communication mechanism for operating a well. Alternatively, electronics can include a communications interface to provide signals output by detectors of the tool 709 to the surface over a standard communication mechanism for operating a well, where these output signals can be analyzed at a processing unit at the surface.

During drilling operations, the drill string 708 can be rotated by the rotary table 707. In addition to, or alternatively, the bottom hole assembly 720 can also be rotated by a motor (e.g., a mud motor) that is located downhole. The drill collars 715 can be used to add weight to the drill bit 726. The drill collars 715 also can stiffen the bottom hole assembly 720 to allow the bottom hole assembly 720 to transfer the added weight to the drill bit 726, and in turn, assist the drill bit 726 in penetrating the surface 704 and subsurface formations 714.

During drilling operations, a mud pump 732 can pump drilling fluid (sometimes known by those of skill in the art as "drilling mud") from a mud pit 734 through a hose 736 into the drill pipe 718 and down to the drill bit 726. The drilling fluid can flow out from the drill bit 726 and be returned to the surface 704 through an annular area 740 between the drill pipe 718 and the sides of the borehole 712. The drilling fluid may then be returned to the mud pit 734, where such fluid is filtered. In some embodiments, the drilling fluid can be used to cool the drill bit 726, as well as to provide lubrication for the drill bit 726 during drilling operations. Additionally, the drilling fluid may be used to remove subsurface formation 714 cuttings created by operating the drill bit 726.

In various embodiments, the tool 709 may be included in a tool body 770 coupled to a logging cable 774 such as, for example, for wireline applications. The tool body 770 containing the tool 709 can include electronics to activate one or more acoustic sources of the tool 709 and collect responses from a detector of the tool 709. Such electronics can include a data unit to provide images and analyzed results to the surface over a standard communication mechanism for operating a well. Alternatively, electronics can include a communications interface to provide signals output by detectors of the tool 709 to the surface over a standard communication mechanism for operating a well, where these output signals can be analyzed at a processing unit at the surface. The logging cable 774 may be realized as a wireline (multiple power and communication lines), a mono-cable (a single conductor), and/or a slick-line (no conductors for power or communications), or other appropriate structure for use in bore hole 712.

Although specific embodiments have been illustrated and described herein, it will be appreciated by those of ordinary skill in the art that any arrangement that is calculated to achieve the same purpose may be substituted for the specific embodiments shown. Various embodiments use permutations and/or combinations of embodiments described herein. It is to be understood that the above description is intended to be illustrative, and not restrictive, and that the phraseology or terminology employed herein is for the purpose of description. Combinations of the above embodiments and other embodiments will be apparent to those of skill in the art upon studying the above description.

What is claimed is:

1. A method comprising:
    acquiring an acoustic wave at a detector, the acoustic wave propagating from a target to the detector, the target being acoustically illuminated to provide the acoustic wave; and
    processing, in a model using a processor, a signal from the detector in response to acquiring the acoustic wave to provide pressure and its spatial derivatives such that the processing implements a synthetic acoustic lens based on the pressure and its spatial derivatives to generate an image of the target.

2. The method of claim 1, wherein the image is formed by calculating acoustic pressure intensity amplitude at a planar cell array near a focal point inside the model and by converting the intensity amplitude to an optical gray scale level.

3. The method of claim 1, wherein acquiring the acoustic wave at the detector includes acquiring the acoustic wave at a planar array of individual pressure sensors.

4. The method of claim 3, wherein the method includes synthesizing a receiver array aperture larger than that of the planar array of individual pressure sensors by physically moving the planar array and repeating acoustic illumination of the target and acquisition of an acoustic wave from the target.

5. The method of claim 1, wherein the method includes:
    operating on the detector such that an incremental offset of the detector relative to the target is generated, the incremental offset relative to the detector when the acoustic wave is acquired;
    acquiring a second acoustic wave at the detector, the second acoustic wave propagating from the target to the detector;
    deriving a velocity wave field based on a pressure gradient calculation using acquired acoustic waves at the detector; and
    applying a pressure wave field of the acoustic wave and the velocity wave field in the processing in the model to generate the image of the target.

6. The method of claim 1, wherein processing includes implementing a plurality of synthetic acoustic lenses of different shapes and contrasts such that target images at different depths of the target are generated.

7. The method of claim 1, wherein the model is structured to have essentially perfect matching boundary layers with a buffering layer through which the acoustic wave propagates from the target to the detector and to have mechanical properties of the buffering layer.

8. The method of claim 1, wherein the method is conducted with respect of an oil or gas drilling operation.

9. A method comprising:
    acquiring an acoustic wave at a detector, the acoustic wave propagating from a target to the detector, the target being acoustically illuminated to provide the acoustic wave; and
    processing, in a model using a processor, a signal from the detector in response to acquiring the acoustic wave such that the processing implements a synthetic acoustic lens to generate an image of the target, wherein the image is formed by calculating acoustic pressure intensity amplitude at a planar cell array near a focal point inside the model and by converting the intensity amplitude to an optical gray scale level, wherein the model is structured as a finite difference model.

10. A method comprising:
    acquiring an acoustic wave at a detector, the acoustic wave propagating from a target to the detector, the target being acoustically illuminated to provide the acoustic wave;
    processing, in a model using a processor, a signal from the detector in response to acquiring the acoustic wave such that the processing implements a synthetic acoustic lens to generate an image of the target;
    using a planar array of individual pressure sensors as the detector to generate a pressure wave field;
    using velocity sensors to directly record a velocity wave field; and
    applying the pressure wave field and the velocity wave field in the processing in the model to generate the image of the target.

11. A machine-readable storage device having instructions stored thereon, which, when executed by a machine, cause the machine to perform operations, the operations comprising:
    acquiring a signal from a detector in response to the detector acquiring an acoustic wave, the acoustic wave propagating from a target to the detector, the target being acoustically illuminated to provide the acoustic wave; and
    processing, in a model using a processor, the signal from the detector in response to acquiring the acoustic wave to provide pressure and its spatial derivatives such that the processing implements a synthetic acoustic lens based on the pressure and its spatial derivatives to generate an image of the target.

12. The machine-readable storage device of claim 11, wherein instructions includes instructions to form the image by calculating acoustic pressure intensity amplitude at a planar cell array near a focal point inside the model and by converting the intensity amplitude to an optical gray scale level.

13. The machine-readable storage device of claim 11, wherein the detector includes a planar array of individual pressure sensors.

14. The machine-readable storage device of claim 13, wherein the instructions include synthesizing a receiver array aperture larger than that of the planar array of individual pressure sensors by physically moving the planar array and repeating the acoustic illumination of the target and acquisition of an acoustic wave from the target.

15. The machine-readable storage device of claim 11, wherein the instructions include:
   operating on the detector such that an incremental offset of the detector relative to the target is generated, the incremental offset relative to the detector when the acoustic wave is acquired;
   acquiring a second acoustic wave at the detector arranged with the incremental offset, the second acoustic wave propagating from the target to the detector;
   deriving a particle velocity wave field based on a pressure gradient calculation based on acquired acoustic waves at the detector; and
   applying a pressure wave field of the acoustic wave and the velocity wave field in the processing in the model to generate the image of the target.

16. The machine-readable storage device of claim 11, wherein processing includes implementing a plurality of synthetic acoustic lenses of different shapes and contrasts such that target images at different depths of the target are generated.

17. The machine-readable storage device of claim 11, wherein the model is structured to have essentially perfect matching boundary layers with a buffering layer through which the acoustic wave propagates from the target to the detector and to have mechanical properties of the buffering layer.

18. A machine-readable storage device having instructions stored thereon, which, when executed by a machine, cause the machine to perform operations, the operations comprising:
   acquiring a signal from a detector in response to the detector acquiring an acoustic wave, the acoustic wave propagating from a target to the detector, the target being acoustically illuminated to provide the acoustic wave; and
   processing, in a model using a processor, the signal from the detector in response to acquiring the acoustic wave such that the processing implements a synthetic acoustic lens to generate an image of the tar et wherein instructions includes instructions to form the image b calculating acoustic pressure intensity amplitude at a planar cell array near a focal point inside the model and by converting the intensity amplitude to an optical gray scale level, wherein the model is structured as a finite difference model.

19. A machine-readable storage device having instructions stored thereon, which, when executed by a machine, cause the machine to perform operations, the operations comprising:
   acquiring a signal from a detector in response to the detector acquiring an acoustic wave, the acoustic wave propagating from a target to the detector, the target being acoustically illuminated to provide the acoustic wave;
   processing, in a model using a processor, the signal from the detector in response to acquiring the acoustic wave such that the processing implements a synthetic acoustic lens to generate an image of the target;
   using a planar array of individual pressure sensors as the detector to generate a pressure wave field;
   using velocity sensors to directly record a velocity wave field; and
   applying the pressure wave field and the velocity wave field in the processing in the model to generate the image of the target.

20. A system comprising:
   a detector to acquire acoustic waves from a target; and
   a data processing unit arranged to process signals from the detector in response to the acquired acoustic waves, the data processing unit arranged to process the signals in a model to provide pressure and its spatial derivatives such that the data processing unit operatively implements a synthetic acoustic lens based on the pressure and its spatial derivatives to generate an image of the target.

21. The system of claim 20, wherein the system includes a source to acoustically illuminate the target.

22. The system of claim 20, wherein the data processing unit is structured to generate the image by operatively calculating acoustic pressure intensity amplitude at a planar cell array near a focal point inside the model and by operatively converting the intensity amplitude to an optical gray scale level.

23. The system of claim 20, wherein the detector includes a planar array of individual pressure sensors.

24. The system of claim 23, wherein the system includes an actuator arranged to physically move the planar array such that the data processing unit is enabled to operatively synthesize a receiver array aperture larger than that of the planar array of individual pressure sensors.

25. The system of claim 23, wherein the system includes an actuator arranged to physically move the planar array to generate an incremental offset of the detector relative to the target such that the data processing unit is enabled to operatively derive a velocity wave field based on a pressure gradient calculation using acquired acoustic waves at the detector and to apply the velocity wave field and a corresponding pressure wave field in the processing in the model to generate the image of the target.

26. The system of claim 20, wherein the data processing unit is structured to implement a plurality of synthetic acoustic lenses of different shapes and contrast to operatively generate target images at different depths of the target.

27. The system of claim 20, wherein the model is structured to have essentially perfect matching boundary layers with a buffering layer through which the acoustic wave propagates from the target to the detector and to have mechanical properties of the buffering layer.

28. The system of claim 20, wherein the detector and the data processing unit are arranged as a logging-while-drilling tool.

29. The system of claim 20, wherein the detector and the data processing unit are arranged as a wireline tool.

30. A system comprising:
   a detector to acquire acoustic waves from a target;
   a data processing unit arranged to process signals from the detector in response to the acquired acoustic waves, the data processing unit arranged to process the signals in a model such that the data processing unit operatively implements a synthetic acoustic lens to generate an image of the target; and
   one or more velocity sensors structured to directly record a velocity wave field to generate the image of the target.

* * * * *

UNITED STATES PATENT AND TRADEMARK OFFICE
CERTIFICATE OF CORRECTION

PATENT NO. : 9,110,166 B2
APPLICATION NO. : 13/309342
DATED : August 18, 2015
INVENTOR(S) : Chang et al.

Page 1 of 1

It is certified that error appears in the above-identified patent and that said Letters Patent is hereby corrected as shown below:

In the claims

In column 11, line 40, in Claim 18, delete "tar et" and insert --target,--, therefor In column 11, line 41, in Claim 18, delete "b" and insert --by--, therefor Signed and Sealed this
Ninth Day of August, 2016

Michelle K. Lee
*Director of the United States Patent and Trademark Office*